United States Patent [19]

O'Donnell, Jr.

[11] Patent Number: 5,288,293
[45] Date of Patent: Feb. 22, 1994

[54] IN VIVO MODIFICATION OF REFRACTIVE POWER OF AN INTRAOCULAR LENS IMPLANT

[76] Inventor: Francis E. O'Donnell, Jr., 709 The Hamptons La., Town & Country, Mo. 63017

[21] Appl. No.: 950,224

[22] Filed: Sep. 24, 1992

[51] Int. Cl.$^5$ .............................................. A61F 2/16
[52] U.S. Cl. ........................................................ 623/6
[58] Field of Search ............................................ 623/6

[56] References Cited

U.S. PATENT DOCUMENTS

| | | | |
|---|---|---|---|
| 4,685,921 | 8/1987 | Peyman | 623/6 |
| 4,731,078 | 3/1988 | Stoy et al. | 623/6 |
| 4,816,031 | 3/1989 | Pfoff | 623/6 |
| 4,906,246 | 3/1990 | Grendahl | 623/6 |
| 4,994,083 | 2/1991 | Sulc et al. | 623/6 |
| 4,997,442 | 3/1991 | Barrett | 623/6 |
| 5,152,788 | 10/1992 | Isaacson et al. | 623/6 |

Primary Examiner—Randall L. Green
Assistant Examiner—Mary Beth O. Jones
Attorney, Agent, or Firm—Paul M. Denk

[57] ABSTRACT

A change is effected in the refractive power (spherical and astigmatical) of an intraocular implant of the type having a lens, either formed of a series of laminates of material, or having a lens that is coated with material, said material, when subject to laser energy providing for its expansion or contraction, and thereby varying the curvature of the lens, and hence, effecting an increase or decrease in its relative refractive index or power. The direction at which the laser energy is applied to the lens can effect the relative change in the refractive power of the lens. A modification provides haptics diametrically or concentrically extending from the optic lens, with a segment of material such as hydrogel or collagen at the juncture between the haptics and the lens, which when directionally exposed to laser energy, can cause an increase or decrease in the relative refractive power of the implanted lens.

1 Claim, 1 Drawing Sheet

IN VIVO MODIFICATION OF REFRACTIVE POWER OF AN INTRAOCULAR LENS IMPLANT

BACKGROUND OF THE INVENTION

This invention relates to in vivo modification of refractive power of an intraocular lens implant, and more specifically, the invention pertains to a method of changing the refractive power of an intraocular lens by the use of laser energy, generally after the lens has been implanted.

It is well accepted that the insertion of an intraocular lens is the best solution for corrective vision after cataract surgery. Intraocular lenses and methods of inserting them are known to the art. For example, the U.S. Pat. No. 4,056,855, to Kelman, discloses an intraocular lens and a method of implanting same through an incision in the eye. The assembly includes a lens member and supporting wire initially in a disassembled condition and adapted to be introduced through a small incision in the eye. U.S. Pat. No. 4,608,049, also to Kelman, discloses an intraocular lens which may be inserted into the eye through a smaller incision in the cornea. U.S. Pat. No. 4,693,716, to MacKool, discloses an intraocular lens and implant including a lens centered on a lens axis. U.S. Pat. No. 4,813,954, to Siepser, discloses a compression, deformation, and dehydration method of fabrication and implantation of an expanse aisle, hydrogel intraocular lens. The problems associated with the foregoing patents include the fact that once the intraocular lens is implanted, it is not possible to change the refractive power of the implanted lens. Thus, when further correction becomes necessary, they must be replaced. U.S. Pat. No. 5,041,134, to O'Donnell, the inventor herein, discloses an intraocular lens assembly for implanting in the posterior chamber of a human eye after an extracapusular extraction. The intraocular lens assembly includes an optic holder having haptic elements for locating and positioning the optic holder in a fixed position within the posterior chamber of the eye and its optic lens releasably secured to the optic holder for interchange of different optic lenses as needed without removing the entire optic holder from the eye. This will allow changing of the refractive index of the implant without removal of the entire implant, but still the lens itself must be replaced. The Schachar U.S. Pat. No. 4,373,281, discloses a variable power intraocular lens and method of implanting same, the lens including a fluid expandable sac, which includes the lens portion, and a valve portion, that extends through sclera of the eye so that the fluid is subject to valve action which apparently can change the fluid expandable sac in order to vary the lens refraction. This patent requires the use of an electrode and microprocessor for changing the index of refraction of the intraocular lens to respond to desired parameters, but does nor disclose the use of the laser to make the fine adjustments in the refractive power of the lens.

U.S. Pat. No. 4,669,466, to L'Esperance, discloses a method and apparatus for the analysis and correction of abnormal refractive errors of the eye. This invention discloses instrumentation for performing refraction-corrective surgery directly to the cornea. U.S. Pat. No. 4,665,913, also to L'Esperance, discloses another related method for ophthalmological surgery using a laser, but is limited to use upon the anterior surface of the cornea of the eye and not an intraocular lens implant. U.S. Pat. No. 4,676,790, to Kern, shows a method of manufacture and implantation of corneal inlays. A laser is used for milling into the surface of the cornea, to form a recess, so that when the implant is applied, its surface lies flush with the corneal membrane. This invention does not utilize lasers for changing the index, but simply provides lasers for use for inlaying an implant within the corneal surface.

Another L'Esperance U.S. Pat. No. 4,718,418, discloses another apparatus for ophthalmological surgery utilizing a laser for contouring the surface of the cornea to eliminate astigmatism and to provide a corneal curvature correction.

The U.S. Pat. No. 4,793,344, to Cumming, et al, discloses a method for preparing corneal donor tissue for refractive eye surgery.

Finally, U.S. Pat. No. 4,923,467, to Thompson, shows an apparatus and process for application and adjustable reprofiling of synthetic lenticules for vision correction. This disclosure defines the process of ablating, by laser, a groove in the cornea, to receive the peripheral edge of the implant lens, and then utilizing the laser to deliver a reprofiling of the lenticule for refining its refractive power.

None of the aforementioned art utilizes laser energy to change the refractive power of an existing lens of the invention. It is therefore, an object of this invention to provide a method of correction of the refractive power of an implanted intraocular implant by using laser energy to alter the refractive power of the implanted lens. Both the spherical and astigmatic power could be modified and, multifocality could be provided.

Another object of the invention is to provide a method of modifying the implant power of an intraocular implant by changing the state of internal hydration of the intraocular implant.

Yet another object of this invention is to provide a method for changing the refractive power of an intraocular implant by using laser energy to collapse the internal layer of the intraocular implant thereby causing a reduction in the frontal curvature.

Still a further object of this invention is to provide a method for changing the refractive power of an intraocular implant by using laser energy to contract an internal layer of the intraocular implant, thereby causing expansion and the increase of curvature of the implant surface, thereby increasing refractive power.

Still another object of this invention is to provide a method for changing the refractive power of an intraocular implant by altering the curvature of the implant by direct surface treatment of the implant with laser energy.

Another object of the present invention is to provide a method of changing the refractive power of the intraocular lens by applying laser energy to modify the haptic-optic angle of the intraocular implant, thereby causing motion of the optic to either increase or decrease the relative refractive power of the optic.

SUMMARY OF THE INVENTION

Briefly stated, this invention relates to a method of changing the refractive index of a intraocular implant in vivo by applying laser energy to the intraocular implant so as to open microfenestrations in the implant, and hence allowing increasing hydration of the internal layer, thereby increasing the front curvature and increasing their refractive power. In another embodiment of the present invention, laser energy is applied to an intraocular implant in vivo to cause the collapse of an internal layer of the implant thereby causing a reduction of the front curvature. Laser energy is applied to an intraocular implant to contract an internal layer of the intraocular implant thereby causing expansion and increased curvature of the surface, increasing refractive power. In another embodiment of the present invention, laser energy is applied directly to the surface of an intraocular implant, thereby changing the curvature of the implant and thereby increasing or decreasing the refractive power of the implant. And, in another embodiment of the present invention, laser energy is applied to the haptic optic angle of a intraocular lens assembly, either causing forward motion of the optic, thereby increasing the relative refractive power, or causing backward motion of the implant causing decrease in the relative refractive power.

This invention contemplates the development of an implant lens which may have its refractive index varied even after it has been implanted into the eye. The variation preferably is done through the use of a laser, which causes an expansion or contraction of select components of the lens, to achieve its index variation. Or, this invention yet recognizes that the refractive power for the intraocular lens may be varied, even before it is implanted into the eye, so that the changes may be made in sito by the ophthalmologist, after determining the extent of correction required to improve the vision of the patient, before the lens implant is made.

The invention utilizes a multicomponent lens, that may be made up of various laminate components, with the front and back layers for the lens being formed of a material such as silicone, collagen, polyacrylamide, a soft PMMA, or the like. The center layer for the lens, arranged intermediately the front and back segments, may be formed of a hydrogel, or other collagen. Thus, it is the change in state of the internal hydration, particularly of the hydrogel component, that causes the lens to vary in shape, and thereby varying the refractive index, to correct for any error in vision, for the patient. Normally, the purpose of this invention is to provide for achieving the correct spherical and cylindrical residual refractive power, after any error has eventually become inherent in the implanted lens, following implant surgery which may have taken place at some previous time, in order to reach that power necessary for the patient to have reasonably clear avoided vision. In addition to the foregoing, in order that the hydrogel layer may have a greater effect in achieving the change in curvature of the lens, during treatment by the laser, the intermediate layer may have a series of upstanding integral columns, arranged around the periphery of the front layer of the lens, so that the increasing of the hydration of the intermediately arranged layer will increase the front curvature of the lens, thereby increasing its refractive power. These upright columns of the hydrogel layer are intended to provide an access for the laser directly to the intermediate segment, and these columns function as a waterproof-membrane covered microfenestrations, that allow access to the said center layer. Thus, through the use of the laser, a collapse may be attained for the internal layer, which causes a reduction in the front curvature, thereby reducing the surface curvature and the refractive power of the lens. To the contrary, the laser energy may be used to contract, or heat up, the internal layer B, to cause its expansion, and increase the curvature of the frontal surface, thereby increasing the refractive power of the lens.

As an alternative, the hydrogel may be located at the junction between the haptic holding the optic lens in place, and when the laser is applied to the arranged hydrogel, or related material, it causes a change in variation in the haptic-optic angle, thereby effecting a change in the implant power. Thus, applying laser energy to, for example, the frontal surface of the juncture may cause a forward motion of the optic, causing its increase in relative refractive power. Applying the laser energy to the backside thereof, may cause a backward motion to the implant, thereby effecting a decrease in its relative refractive power. These are examples as to how the optics of the intraocular lens may be varied, to cause a variation and modification in its refractive power, so as to improve the vision of the patient in whom the lens has been previously implanted, but requires a variation in the same, either immediately after surgery, so as to fine tune the viewing by the patient through the newly implanted lends, or at some subsequent date, when a corrective variation in the refractive power of the lens becomes necessary in order to further improve vision.

Variations in this concept for providing means for varying the refractive power of an intraocular lens, either before the lens is implanted, or preferably after it has been implanted by the physician, may occur to those skilled in the art upon reviewing the summary of the invention, in addition to undertaking a study of the description of its preferred embodiment, in light of the drawings.

BRIEF DESCRIPTION OF THE DRAWINGS

In referring to the drawings, FIG. 1 provides a schematic side view showing the laminations for the intraocular lens of this invention.

DESCRIPTION OF THE PREFERRED EMBODIMENT

As previously reviewed, the concept of this invention is to allow usage of a laser device to modify the curvature, either at the front or back, of an optic lens, of the implant type, which may be fabricated from material that is subjected to degrees of hydration, whether the lens be formed totally or partially of a silicone, hydrogel, PMMA, collagen, or the like. Preferably, the modification can be made after the intraocular lens has been implanted or inserted into the eye.

More specifically, this concept is to provide a way to fine tune the refractive power of the implant in vivo. The laser energy utilized could be at any normal and usable wave length such as 1064 nanometer, with the laser being directed and aimed at the surface, either the front or back, of the implant optic, or at its intermediate lamination, with the purpose of changing the curvature, and as a result, the refractive power of the implanted lens. In general, the implant lens might be coated with an inert surface material to facilitate a surface curvature change when exposed to the effect of the laser. This surface might be enclosed in order to confine resultant debris. Alternatively, the laser energy could be aimed at the haptic-lens implant junction, to alter the anterior-posterior position of the implant, relative to its haptic, and thus change the residual refractive error of the eye. Normally, the more anterior the location of the optic, the less plus power refractive power variation or change will be necessary.

Finally, the implant could be used to altar the states of hydration of the optic and thus change the shape and hence the refractive power of the implant, through laser application.

Figure 1:
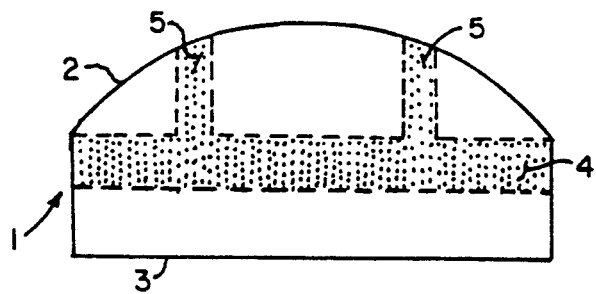
Figure 2:
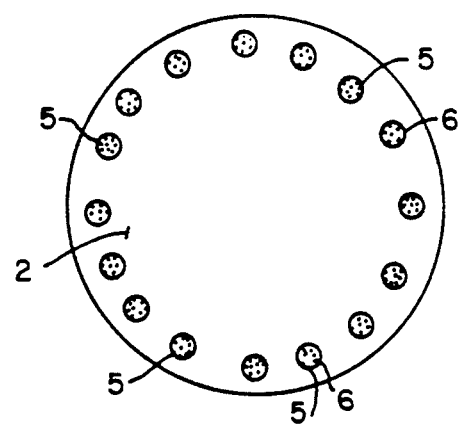
FIG. 2 is a top plan view thereof.

More specifically, in referring to FIG. 1, a schematic is provided of the type of implant lens that may be used in this invention, the lens being shown at 1. It may include a series of of laminations, wherein a frontal and curved section of the lens that adds the refractive power to it, is shown at 2, while the posterior lamination 3 may be formed of the same material. Generally, various types of compositions that may be formed into these frontal and back laminations may include silicone, a collagen, a polyacryalmide, or a soft PMMA, or the like. The essence of the invention, though, is to provide a layer of material, generally intermediately disposed, as can be seen at 4, and which is designed to provide for an increasing in the hydration of said layer, when exposed to laser energy, whereby the laser may be used to open the microfenestrations of the material forming this intermediate layer, to thereby increase the front curvature of the lens, and thereby enhance the refractive power of the implant. This increasing of hydration, through exposure of the intermediate layer to laser energy, enhances its hydration, to thereby force the frontal layer into a greater curvature, to add to the plus power of the refractive index for the constructed lens. As can be further seen, and as shown in FIG. 2, the intermediate layer 4, which may be formed of a hydrogel or collagen, may have upwardly extending columns, as at 5, that extend through the anterior laminate 2, so as to provide a path for direction of the laser energy, to increase the hydration of the column 5 segments, but also to focus the laser energy into the hydrogel layer 4, as previously explained. Generally, the columns 5, while formed of the hydrogel or collagen type material, which may be subject to increased hydration, when exposed initially to laser energy, may be lined or covered with a waterproof-membrane, as at 6, so as to focus the laser energy in its direction upon the hydrogel material itself making up the laminate B, and its integral columns 5.

Figure 3:
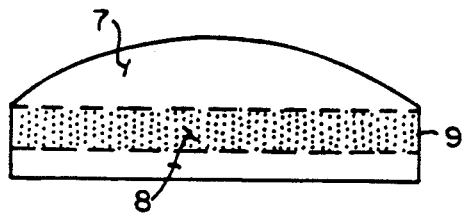
FIG. 3 is a schematic side view of a modification to the lens of FIG. 1.

As can be seen in FIG. 3, which shows a slight modification to the method of fabricating the intraocular lens, it includes similar type of layers making up the laminate of FIG. 1, wherein the anterior and posterior layers 7 and 8, respectively, may be formed of the same composition as previously described. The intermediate laminate 9 will likewise be formed of a layer of material such as hydrogel or collagen that may have increased hydration when exposed to the initial laser energy. But, when further exposed to laser energy, such that evaporation of some moisture of the hydrogel layer 9 may be encountered, there may be a collapse of the layer 9, which causes a reduction in the front curvature of the lens, and therefore, the inducement of a lessening of the refractive index of the formed lens. This provides a correction in the focal power of the lens but in an opposite direction. The laser energy is used to collapse the internal layer, thereby reducing the surface curvature of the anterior lens 7, and thereby reducing its refractive power. When the laser energy is initially used to contact the intermediate layer 9, its energy will heat up this intermediate layer B, causing an expansion and increase in the curvature of the anterior lens 7, thereby increasing the refractive power of the implant lens.

Figure 4:
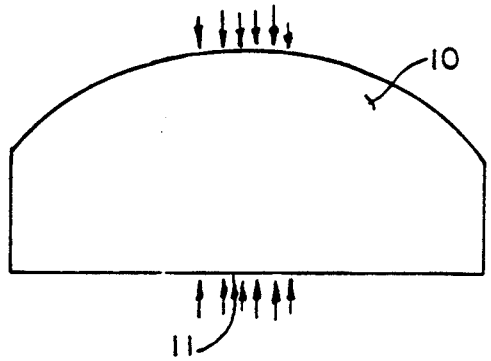
FIG. 4 is a schematic side view of the lamination of the lens of FIG. 1.

FIG. 4 discloses a side view of an anterior lens, similar to that as previously reviewed with respect to the lens laminate 2 of FIG. 1, and the laminate 7 of FIG. 2. The material forming the anterior lens 10 will likewise be of a silicone, collagen, polyacrylamide, or soft PMMA, or the like. The impingement of the laser energy directly onto the lens 10 attains a focal point at its back surface, approximately at the location 11, and may have a tendency to initially heat up and expand the lens layer 10, to cause an increase in its refractive power, or after continuing exposure of the material to the laser energy, may cause a reduction in its moisture content, and a consequential collapse of its interior layer, thereby reducing the refractive power of the implant lens. On the other hand, by directing the laser energy onto the front surface of the lens 10, this may tend to increase its curavature, and thereby increase its refractive power, or by directing the laser energy onto the back surface of the lens 10, causing a reduction in its front curvature, thereby decreasing the refractive power of the intraocular lens. These are examples as to how laser energy may be applied to an implant lens, or various laminates forming it, and which has an effect upon its hydration, to very its shape or curvature, and consequently, its refractive power.

Furthermore, the implant lens may have a special coating upon it, to facilitate this change of curvature, when exposed to laser energy. For example, a PMMA optic coated with silicone, collagen, or hydrogel, may have greater susceptibility to hydrate, or dehydrate, when exposed at various locations to the laser energy, to thereby change its shape, and hence its refractive power.

It is also likely that the technique of intrastromal or surface laser modification, as explained in the examples above, could also be applied to injectable implants, of the type that are used to replace a lens of the eye, after a cataract removal. Injectable implants are designed to fill the capsular bag after endocapsular removal of the cataract has been performed through surgery.

Figure 5:
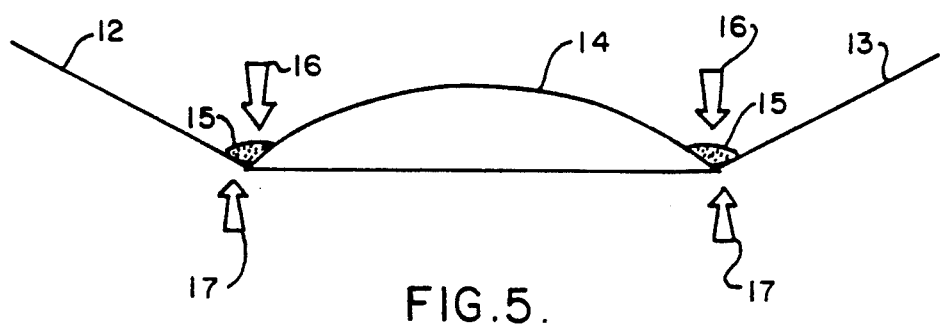
FIG. 5 discloses a lens with haptics showing a modification in the method for attaining variation in the refractive power of a lens.
Figure 6:
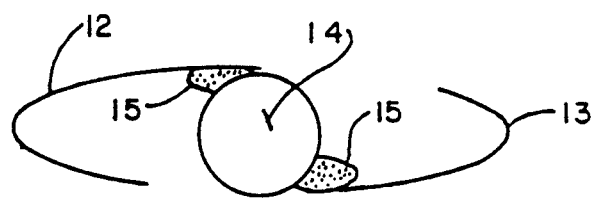
FIG. 6 is a front view thereof.

A further modification to the subject matter of this invention, whereby the optic lens may have its refractive index varied, even after it had been previously implanted, can be seen in FIGS. 5 and 6. In this particular instance, there may be a material that is formed at the juncture between the haptic, such as those shown at 12 and 13, and which connect to the implant lens 14. At this juncture there may be located the material 15 that may be more readily subjectable to hydration, or dehydration, such as the type of hydrogel or collagen as previously explained. Thus, modifying the haptic-optic angle, through laser energy treatment, provides for an effect in the change in the implant power. Thus, applying laser energy from the front of the lens, as can be seen from the direction 16, may have a tendency to cause the optic to move forwardly, and thereby increase its relative refractive power, as may be required. On the other hand, applying the thermal laser energy, or laser treatment, from the rear, as in the direction of the arrow 17, may cause a backward motion to the implant, thereby effecting a decrease in its relative refractive power, and a lessening of its refractive index, as may be further required for viewing correction. These are just examples as to how the optic lens, and its location, or its shape or configuration, may be varied by treatment with thermal laser energy, to inherently effect the refractive power of the implanted lens, even at a subsequent date, in order to provide further correction to the patient's ability to view.

Variations or modifications to the subject matter of this invention may occur to those skilled in the art upon reviewing the subject matter herein. Such variations or modifications, if within the spirit of this invention, are intended to be encompassed within the scope of any claims to patent protection issuing upon this development. The description of the preferred embodiment set forth herein, and its variations, are provided for illustrative purposes only.

Having thus described the invention what is claimed and desired to be secured by Letters Patent is:

1. An intraocular lens implant capable of having its refractive power changed, even after the lens has been formed, including said lens comprising three laminates, said laminates formed as a front, a back, and an intermediate laminate for the lens, at least one of the laminates having curvature for providing the refractive power for correcting viewing through the lens, and at least a second of said laminates formed to provide for a change in the refractive power of the lens by being hydrated and dehydrated when exposed to laser energy, the front and the back laminates formed of one of a silicone, collagen, polyacryalmide, and soft PMMA, with the intermediate laminate formed of one of a hydrogel and collagen, a series of columns extending through the front laminate, said columns being formed of the same material as the intermediate laminate and being formed so as to join with the intermediate laminate.

* * * * *